(12) United States Patent
Kiani et al.

(10) Patent No.: US 10,588,556 B2
(45) Date of Patent: *Mar. 17, 2020

(54) NON-INVASIVE PHYSIOLOGICAL SENSOR COVER

(71) Applicant: MASIMO CORPORATION, Irvine, CA (US)

(72) Inventors: Abraham Mazda Kiani, San Juan Capistrano, CA (US); Massi Joe E. Kiani, Laguna Niguel, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,393

(22) Filed: May 1, 2018

(65) Prior Publication Data

US 2019/0000362 A1    Jan. 3, 2019

Related U.S. Application Data

(63) Continuation of application No. 15/046,954, filed on Feb. 18, 2016, now Pat. No. 9,980,667, which is a
(Continued)

(51) Int. Cl.
*A61B 5/1455* (2006.01)
*A61B 5/024* (2006.01)
(Continued)

(52) U.S. Cl.
CPC ...... *A61B 5/14552* (2013.01); *A61B 5/02416* (2013.01); *A61B 5/02427* (2013.01);
(Continued)

(58) Field of Classification Search
None
See application file for complete search history.

(56) References Cited

U.S. PATENT DOCUMENTS

| 4,796,633 A | 1/1989 | Zwirkoski |
| 4,960,128 A | 10/1990 | Gordon et al. |

(Continued)

FOREIGN PATENT DOCUMENTS

WO    WO 98/43071    10/1998

OTHER PUBLICATIONS

Nov. 8, 2018 Complaint for (1) Breach of Contract (2) Trade Secret Misappropriation (3) Breach of Fiduciary Duty and (4) Patent Infringement and Demand for Jury Trial, *Masimo Corporation and Cercacor Laboratories, Inc.* v. *True Wearables, Inc. and Marcelo Lamego*, Case No. 8:18-cv-2001.
(Continued)

*Primary Examiner* — Clayton E. LaBalle
*Assistant Examiner* — Leon W Rhodes, Jr.
(74) *Attorney, Agent, or Firm* — Knobbe Martens Olson & Bear LLP

(57) ABSTRACT

A sensor cover according to embodiments of the disclosure is capable of being used with a non-invasive physiological sensor, such as a pulse oximetry sensor. Certain embodiments of the sensor cover reduce or eliminate false readings from the sensor when the sensor is not in use, for example, by blocking a light detecting component of a pulse oximeter sensor when the pulse oximeter sensor is active but not in use. Further, embodiments of the sensor cover can prevent damage to the sensor. Additionally, embodiments of the sensor cover prevent contamination of the sensor.

13 Claims, 11 Drawing Sheets

Related U.S. Application Data continuation of application No. 14/512,945, filed on Oct. 13, 2014, now Pat. No. 9,295,421, which is a continuation of application No. 13/919,692, filed on Jun. 17, 2013, now Pat. No. 8,886,271, which is a continuation of application No. 12/844,720, filed on Jul. 27, 2010, now Pat. No. 8,473,020.

(60) Provisional application No. 61/229,682, filed on Jul. 29, 2009.

(51) Int. Cl.
*A61B 5/00* (2006.01)
*A61B 5/145* (2006.01)

(52) U.S. Cl.
CPC ...... *A61B 5/14532* (2013.01); *A61B 5/14546* (2013.01); *A61B 5/6816* (2013.01); *A61B 5/6819* (2013.01); *A61B 5/6826* (2013.01); *A61B 5/6829* (2013.01); *A61B 5/6838* (2013.01); *A61B 5/68335* (2017.08)

(56) References Cited

U.S. PATENT DOCUMENTS

| | | |
|---|---|---|
| 4,964,408 A | 10/1990 | Hink et al. |
| 4,972,829 A | 11/1990 | Knerr |
| 5,041,187 A | 8/1991 | Hink et al. |
| 5,069,213 A | 12/1991 | Polczynski |
| 5,083,868 A * | 1/1992 | Anderson ............ G01N 21/251 356/402 |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| 5,368,025 A | 11/1994 | Young et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,490,523 A | 2/1996 | Isaacson et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,619,992 A | 4/1997 | Guthrie et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,746,694 A | 5/1998 | Wilk et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,797,841 A | 8/1998 | Delonzor et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,902,246 A | 5/1999 | McHenry et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,502 A | 4/2000 | Eppstein et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,140,549 A | 10/2000 | Pompei, Jr. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,179,159 B1 | 1/2001 | Gurley |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,270,460 B1 | 8/2001 | McCartan et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |

(56) References Cited

U.S. PATENT DOCUMENTS

| | | | |
|---|---|---|---|
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,671,532 B1 | 12/2003 | Fudge et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,748,254 B2 | 6/2004 | O'Neil et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,882,873 B2 | 4/2005 | Samuels et al. |
| 6,898,452 B2 | 5/2005 | Al-Ali et al. |
| 6,920,345 B2 * | 7/2005 | Al-Ali ............... A61B 5/14552 600/344 |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,941,162 B2 | 9/2005 | Fudge et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,190,986 B1 | 3/2007 | Hannula et al. |
| 7,190,987 B2 | 3/2007 | Lindekugel et al. |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,386,334 B2 | 6/2008 | DeLonzor et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,486,977 B2 | 2/2009 | Sweitzer et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,574,245 B2 | 8/2009 | Arizaga Ballesteros |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |

(56) References Cited

U.S. PATENT DOCUMENTS

| | | |
|---|---|---|
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,182,487 B2 * | 5/2012 | Milijasevic ............ A61F 2/4611 606/86 A |
| 8,185,180 B2 | 5/2012 | Diab et al. |
| 8,188,433 B2 | 5/2012 | Gonopolskiy et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,328 B2 * | 1/2013 | Mannheimer ........ A61B 5/6843 600/310 |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |

(56) References Cited

U.S. PATENT DOCUMENTS

| | | | |
|---|---|---|---|
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 * | 11/2014 | Kiani .................. A61B 5/14552 600/344 |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 * | 3/2016 | Kiani .................. A61B 5/14552 |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |

(56) References Cited

U.S. PATENT DOCUMENTS

| | | |
|---|---|---|
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,188,331 B1 | 1/2019 | Kiani et al. |
| 10,194,848 B1 | 2/2019 | Kiani et al. |
| 2006/0094943 A1 | 5/2006 | Van Slyke |
| 2006/0161054 A1 | 7/2006 | Reuss et al. |
| 2007/0073121 A1 | 3/2007 | Hoarau et al. |
| 2007/0282478 A1 | 12/2007 | Al-Ali et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0249502 A1* | 9/2010 | Karasawa ............ A61B 1/0008 600/109 |
| 2011/0082711 A1 | 4/2011 | Poeze et al. |
| 2011/0125060 A1 | 5/2011 | Telfort et al. |
| 2011/0208015 A1 | 8/2011 | Welch et al. |
| 2011/0230733 A1 | 9/2011 | Al-Ali |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0182154 A1 | 7/2015 | Kiani et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |

(56) References Cited

U.S. PATENT DOCUMENTS

| | | |
|---|---|---|
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |

OTHER PUBLICATIONS

May 15, 2019 Defendants True Wearables, Inc.'s and Marcelo Lamego's Preliminary Invalidity Contentions, *Masimo Corporation and Cercacor Laboratories, Inc.* v. *True Wearables, Inc. and Marcelo Lamego*, Case No. 8:18-cv-2001-JVS-JDE.

New, William, Jr., "Continuous Non-Invasive Measurement of Arterial Oxygen", Journal of Japan Society for Clinical Anesthesia, vol. 6, No. 6, pp. 460-468 (Dec. 15, 1986).

Nov. 8, 2018 Complaint for (1) Breach of Contract (2) Trade Secret Misappropriation (3) Breach of Fiduciary Duty and (4) Patent Infringement and Demand for Jury Trial, *Masimo Corporation and Cercacor Laboratories, Inc.* v. *True Wearables, Inc. and Marcelo Lamego*, Case No. 8:18-cv-02001, 46 pages.

Dec. 3, 2018 Defendants True Wearables, Inc. and Marcelo Lamego's Answer and Counterclaims to Plaintiffs Masimo Corporation and Cercacor Laboratories, Inc.'s Complaint for (1) Breach of Contract (2) Trade Secret Misappropriation (3) Breach of Fiduciary Duty and (4) Patent Infringement, and Demand for Jury Trial, *Masimo Corporation and Cercacor Laboratories, Inc.* v. *True Wearables, Inc. and Marcelo Lamego*, Case No. 8:18-cv-02001-JVS-JDE, 24 pages.

Dec. 19, 2018 Plantiffs Masimo Corporation and Cercacor Laboratories, Inc.'s Reply to Defendants' Counterclaims, *Masimo Corporation and Cercacor Laboratories, Inc.* v. *True Wearables, Inc. and Marcelo Lamego*, Case No. 8:18-cv-02001-JVS-JDE, 4 pages.

May 15, 2019 Defendants True Wearables, Inc.'s and Marcelo Lamego's Preliminary Invalidity Contentions, *Masimo Corporation and Cercacor Laboratories, Inc.* v. *True Wearables, Inc. and Marcelo Lamego*, Case No. 8:18-cv-02001-JVS-JDE, 88 pages.

Jun. 17, 2019 First Amended Complaint for (1) Breach of Contract (2) Trade Secret Misappropriation (3) Breach of Fiduciary Duty and (4) Patent Infringement, and Demand for Jury Trial, *Masimo Corporation and Cercacor Laboratories, Inc.* v. *True Wearables, Inc. and Marcelo Lamego*, Case No. 8:18-cv-02001-JVS-JDE, 52 pages.

(56) References Cited

OTHER PUBLICATIONS

Jul. 1, 2019 Defendants True Wearables, Inc. and Marcelo Lamego's Answer and Counterclaims to Plaintiffs Masimo Corporation and Cercacor Laboratories, Inc.'s First Amended Complaint for (1) Breach of Contract (2) Trade Secret Misappropriation (3) Breach of Fiduciary Duty and (4) Patent Infringement, and Demand for Jury Trial, *Masimo Corporation and Cercacor Laboratories, Inc.* v. *True Wearables, Inc. and Marcelo Lamego*, Case No. 8:18-cv-2001-JVS-JDE, 36 pages.
Jul. 12, 2019 Plaintiffs Masimo Corporation and Cercacor Laboratories, Inc.'s Reply to Defendants' Counterclaims, *Masimo Corporation and Cercacor Laboratories, Inc.* v. *True Wearables, Inc. and Marcelo Lamego*, Case No. 8:18-cv-2001-JVS-JDE, 10 pages.
U.S. Appl. No. 16/422,874, filed May 24, 2019, Non-Invasive Physiological Sensor Cover.
U.S. Pat. No. 8,983,564, U.S. Appl. No. 16/230,153.
U.S. Pat. No. 8,886,271, U.S. Appl. No. 15/968,393.
U.S. Pat. No. 8,886,271, U.S. Appl. No. 16/422,874.
U.S. Pat. No. 7,295,866, U.S. Appl. No. 15/820,082.
U.S. Pat. No. 7,295,866, U.S. Appl. No. 16/174,130.
U.S. Pat. No. 7,295,866, U.S. Appl. No. 16/174,144.
U.S. Pat. No. 10/194,847, U.S. Appl. No. 16/459,378.
U.S. Pat. No. 10,194,848, U.S. Appl. No. 16/422,874.
U.S. Appl. No. 16/174,130.
U.S. Appl. No. 16/174,144.
Apr. 1, 2019 Plaintiff Masimo Corporation's Infringement Contentions, *Masimo Corporation and Cercacor Laboratories, Inc.* v. *True Wearables, Inc. And Marcelo Lamego*, Case No. 8:18-cv-02001-JVS-JDE, 98 pages.
Jul. 12, 2019 Plaintiff Masimo Corporation's Amended Infringement Contentions, *Masimo Corporation and Cercacor Laboratories, Inc.* v. *True Wearables, Inc. And Marcelo Lamego*, Case No. 8:18-cv-02001-JVS-JDE, 153 pages.
Aug. 16, 2019 Defendants True Wearables, Inc.'s and Marcelo Lamego's Amended Preliminary Invalidity Contentions, *Masimo Corporation and Cercacor Laboratories, Inc.* v. *True Wearables, Inc. And Marcelo Lamego*, Case No. 8:18-cv-02001-JVS-JDE, 178 pages.
Sep. 20, 2019 Plaintiffs Masimo Corporation and Cercacor Laboratories, Inc.'s Preliminary Claim Constructions and Extrinsic Evidence, *Masimo Corporation and Cercacor Laboratories, Inc.* v. *True Wearables, Inc. And Marcelo Lamego*, Case No. 8:18-cv-02001-JVS-JDE, 40 pages.
Oct. 18, 2019 Joint Claim Construction and Prehearing Statement Pursuant to Patent Local Rule 4-3, *Masimo Corporation and Cercacor Laboratories, Inc.* v. *True Wearables, Inc. And Marcelo Lamego*, Case No. 8:18-cv-02001-JVS-JDE, 41 pages.

\* cited by examiner

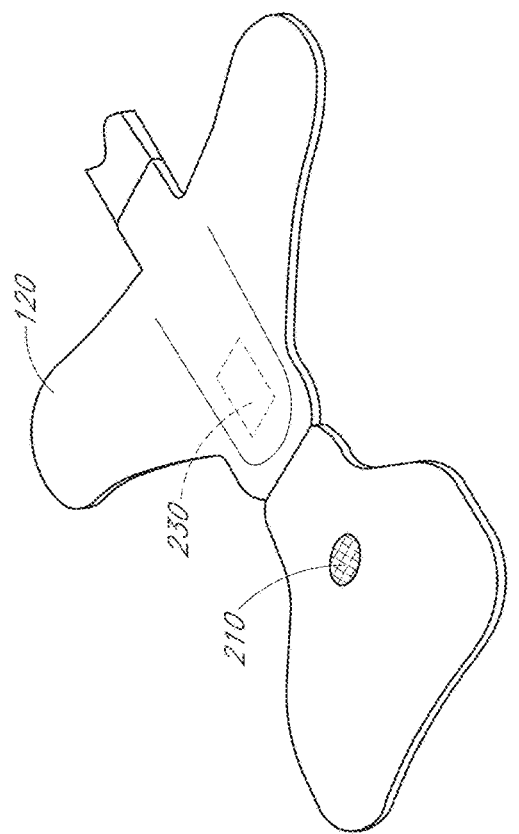
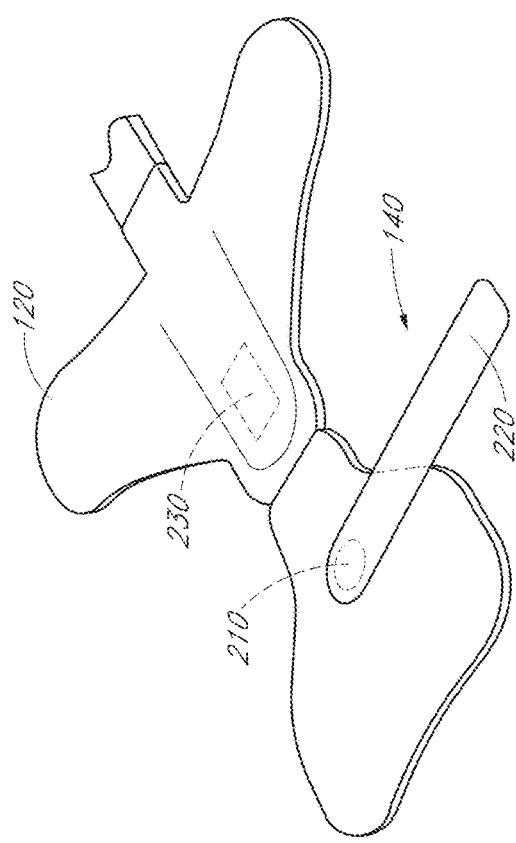

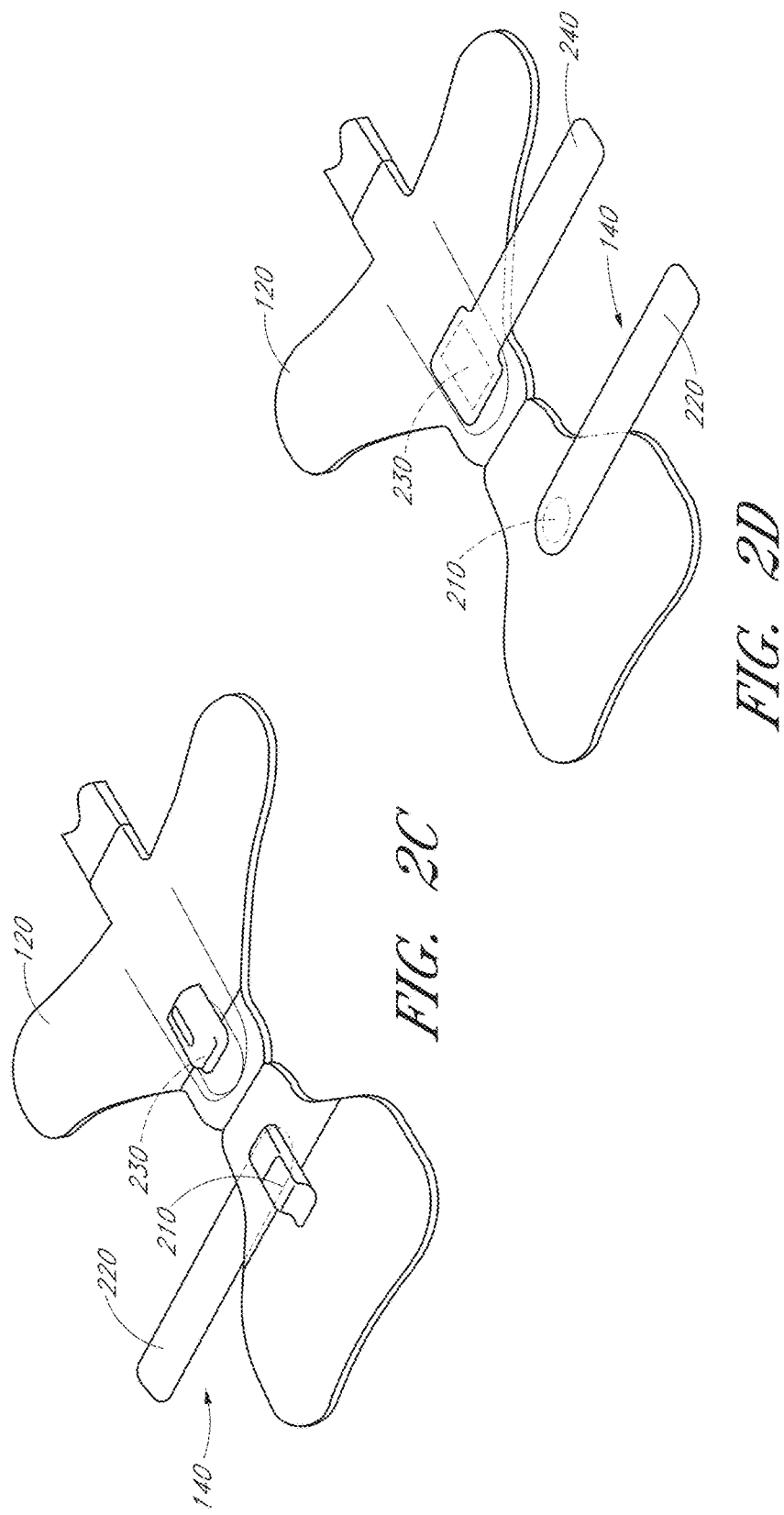

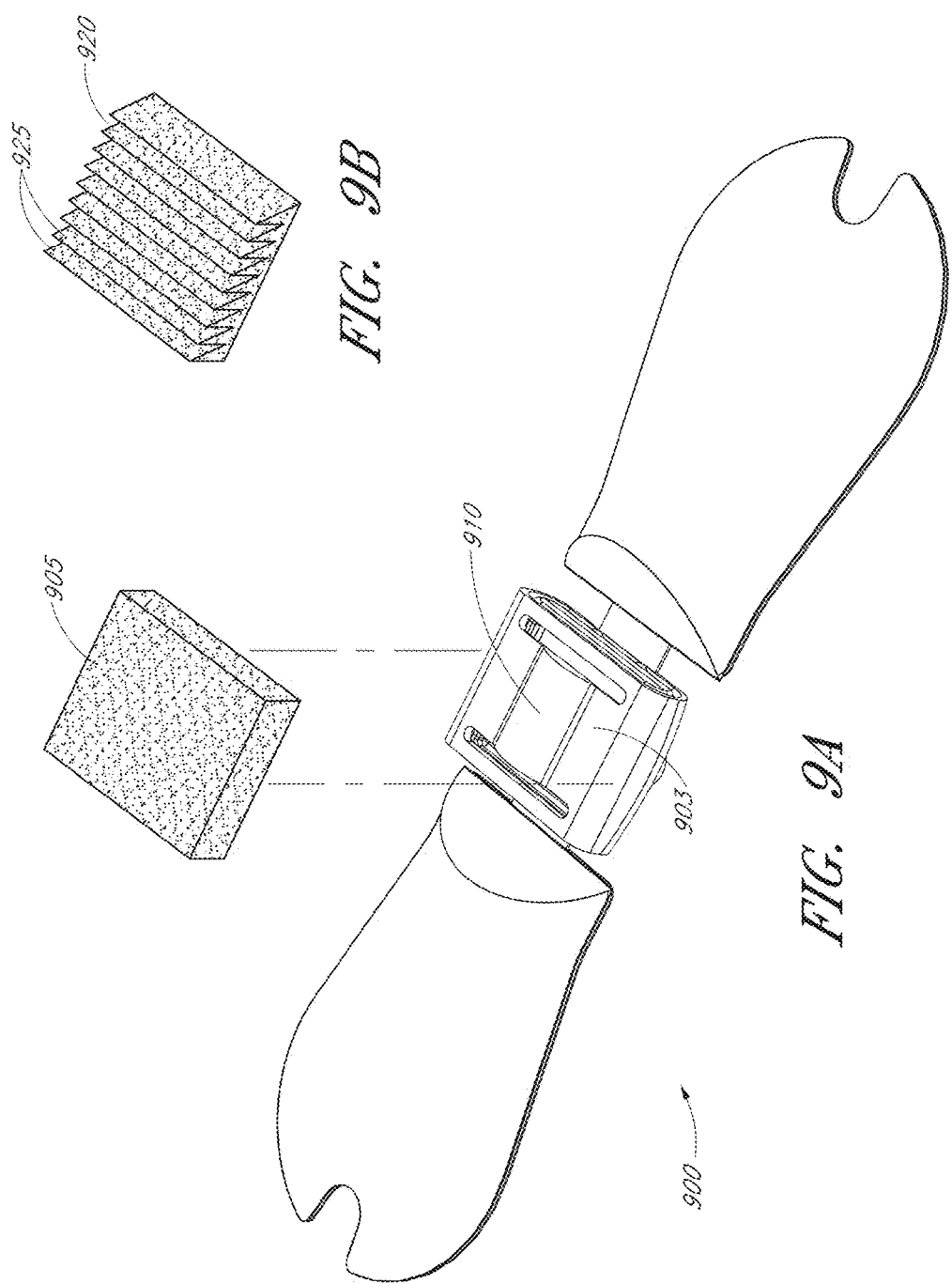

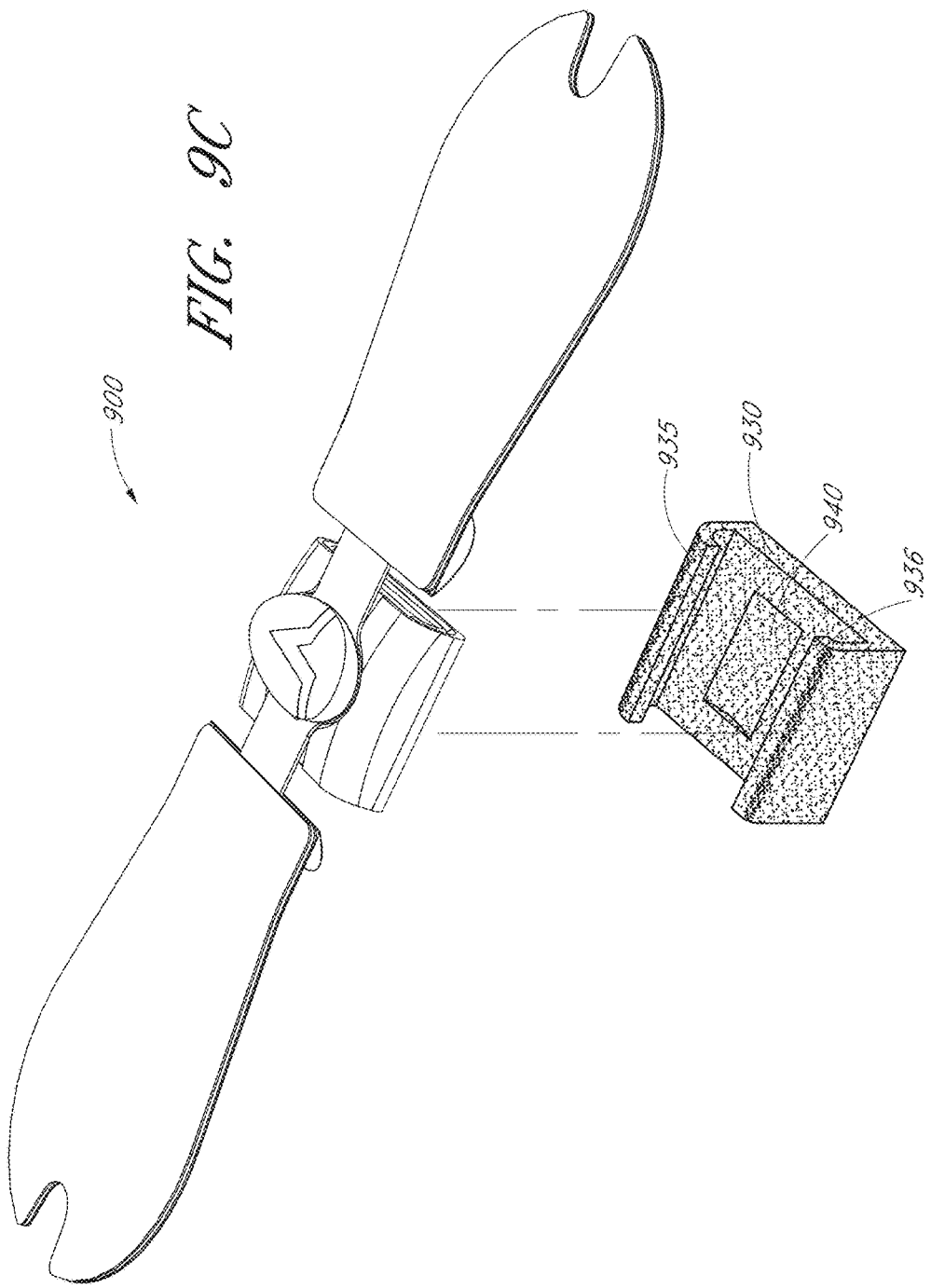

NON-INVASIVE PHYSIOLOGICAL SENSOR COVER

CROSS-REFERENCE TO RELATED APPLICATIONS

The present application is a continuation of U.S. patent application Ser. No. 15/046,954, filed Feb. 18, 2016, titled "NON-INVASIVE PHYSIOLOGICAL SENSOR COVER," which is a continuation of U.S. patent application Ser. No. 14/512,945, filed Oct. 13, 2014, titled "NON-INVASIVE PHYSIOLOGICAL SENSOR COVER," which is a continuation of U.S. patent application Ser. No. 13/919,692, filed Jun. 17, 2013, titled "NON-INVASIVE PHYSIOLOGICAL SENSOR COVER," which is a continuation of U.S. patent application Ser. No. 12/844,720, filed Jul. 27, 2010, titled "NON-INVASIVE PHYSIOLOGICAL SENSOR COVER," which claims priority benefit under 35 U.S.C. § 119(e) from U.S. Provisional Application No. 61/229,682, filed Jul. 29, 2009, titled "Non-invasive Physiological Sensor Cover." All of the above referenced applications are hereby incorporated by reference herein in their entireties.

FIELD OF THE DISCLOSURE

The present invention relates to a sensor for measuring oxygen content in the blood, and, in particular, relates to an apparatus and method for preventing sensor activity when the sensor is not in use.

BACKGROUND OF THE DISCLOSURE

Non-invasive physiological sensors are applied to the body for monitoring or making measurements indicative of a patient's health. One application for a non-invasive physiological sensor is pulse oximetry, which provides a noninvasive procedure for measuring the oxygen status of circulating blood. Oximetry has gained rapid acceptance in a wide variety of medical applications, including surgical wards, intensive care and neonatal units, general wards, and home care and physical training. A pulse oximetry system generally includes a patient monitor, a communications medium such as a cable, and a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and pulse rate.

High fidelity pulse oximeters capable of reading through motion induced noise are disclosed in U.S. Pat. Nos. 6,770,028, 6,658,276, 6,157,850, 6,002,952 5,769,785, and 5,758,644, which are assigned to Masimo Corporation ("Masimo") and are incorporated by reference herein. Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), total Hematocrit (Hct), oxygen concentrations and glucose concentrations, as a few examples. Advanced physiological monitors and corresponding multiple wavelength optical sensors capable of measuring parameters in addition to $SpO_2$, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring $SpO_2$, pulse rate, perfusion index (PI), signal quality (SiQ), pulse variability index (PVI), HbCO and HbMet, among other parameters, are also commercially available from Masimo.

SUMMARY OF THE DISCLOSURE

Optical sensors are widely used across clinical settings, such as operating rooms, emergency rooms, post anesthesia care units, critical care units, outpatient surgery and physiological labs, to name a few. In some situations, such as in operating rooms, emergency rooms or critical care units, sensors can be kept attached to monitors to reduce the setup time needed to begin monitoring a patient. While attached, the sensor can generate false readings by detecting ambient light even though the sensor is not in use. The sensor can also cause the monitor to emit alarms or otherwise make noise due to false readings, which can be distracting to medical personnel.

As such, a method and apparatus for preventing false readings are desirable. A sensor cover, according to embodiments of the disclosure, prevents or reduces false readings until the sensor is in use.

Further, in certain embodiments, the sensor cover can prevent damage to the sensor. For example, the sensors cover can protect the emitters and the detector during shipment or prior to use. In certain embodiments, a sensor cover decreases the likelihood of contamination by keeping covered portions of the sensor clean. Sensors in hospitals and other clinical environments are subject to exposure to infectious agents, dust or other foreign matter from depositing on the emitters or detector. The sensor cover can reduce or prevent exposure to these contaminants.

BRIEF DESCRIPTION OF THE DRAWINGS

FIGS. 2A-2C are top cover-attached, top cover-detached, and bottom cover-attached perspective views, respectively, of the sensor cover and sensor of FIG. 1;

FIG. 2D illustrates a first and second sensor covers over the emitters and detector according to an embodiment of the disclosure;

FIGS. 9A-9D illustrates embodiments of the sensor covers configured for attachment to a bioacoustic sensor, according to embodiments of the disclosure.

DETAILED DESCRIPTION OF THE PREFERRED EMBODIMENT

A sensor cover according to embodiments of the disclosure is capable of being used with a non-invasive physiological sensor. Certain embodiments of the sensor cover reduce or eliminate false readings from the sensor when the sensor is not in use. Further, embodiments of the sensor cover can prevent damage to the sensor. Additionally, embodiments of the sensor cover prevent contamination of the sensor.

The tissue site of the illustrated embodiments is a finger and the following description therefore refers specifically to the tissue site as a finger for the purposes of clarity. This is not intended to be limiting and, as described herein, the sensor cover of certain embodiments can be used with sensors attachable to other types of tissue sites, such as a toe, ear lobe, nose, hand, foot, forehead or the like.

Figure 1:
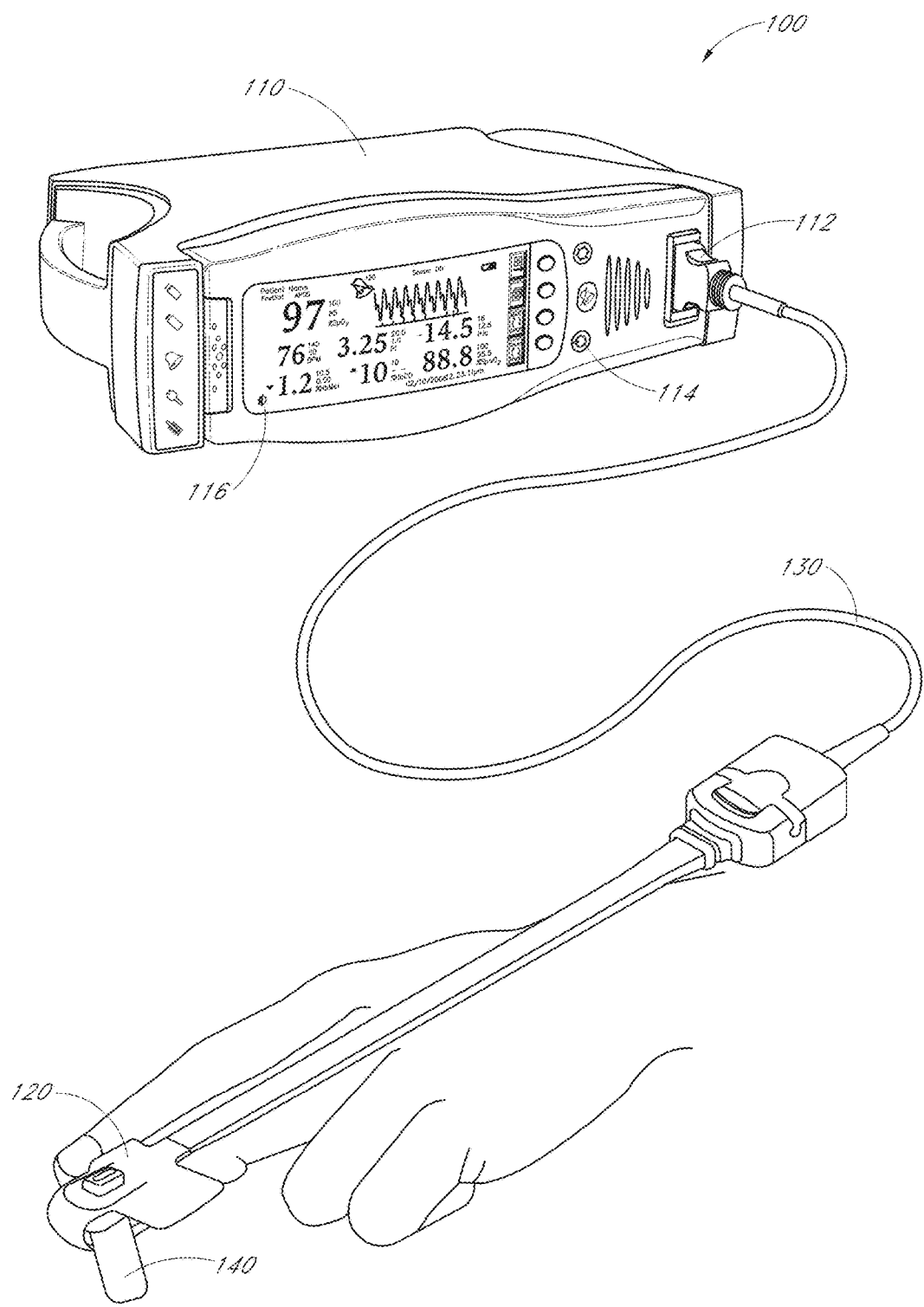
FIG. 1 illustrates a sensor cover attached to a sensor of a physiological measurement system according to an embodiment of the disclosure.

FIG. 1 illustrates an embodiment of a sensor cover attached to a physiological measurement system 100 having a monitor 110 and an optical sensor 120. The optical sensor 120 comprises one or more light emitters and a detector. The optical sensor 120 is configured to plug into a monitor sensor port 112 via a patient cable 130. Monitor keys 114 provide control over operating modes and alarms, to name a few. A display 116 provides readouts of measured parameters, such as oxygen saturation, pulse rate, HbCO, HbMet and Hbt to name a few. Other blood parameters that can be measured to provide important clinical information are fractional oxygen saturation, bilrubin and blood glucose, to name a few.

In the illustrated embodiment of FIG. 1, the sensor cover 140 protrudes outside the sensor. The cover can be made from an opaque material, such as, for example, plastic, polyester, polypropylene, rubber, vinyl, cling vinyl and/or the like. The sensor cover 140 can obstruct the detector and prevent the detector from detecting light, thereby reducing or eliminating false readings. For example, the sensor 120 can sometimes be left attached to a monitor 110 to facilitate quick monitoring of a patient, even when not currently in use. The opaque cover 140 can prevent or reduce false readings caused by the emitters or the ambient light, even if the sensor is active, by preventing the sensor from receiving light. In an embodiment, the opaque material can block all wavelengths of light used by a particular sensor. Other embodiments can block different ranges of wavelengths depending on the type of sensor the cover is used for. In an embodiment, the sensor cover 140 is placed over the emitters to prevent the sensor from emitting light receivable by the detector. In an embodiment, both the detector and emitter are covered.

In some embodiments, the sensor cover 140 can be removed before placement at a measurement site. For example, once a patient arrives, medical personnel can remove the sensor cover 140 and attach the now fully operational sensor 120 to the patient. In some embodiments, the medical personnel can attach the sensor 120 with the cover 140 still in place. The opaque cover prevents measurements from being taken until the sensor 120 is generally secure and the medical personnel are ready to take measurements. For example, movement can generate artifacts for some sensors; therefore waiting until the patient is stable can reduce measurement of inaccurate data. Once the sensor 120 is generally secured to an attachment site, the cover 140 can be removed from the sensor. In some embodiments, the sensor cover 140 can be removed before and/or after placement at a measurement site. The sensor cover 140 can be removed by peeling it off from the sensor or by pulling on the protruding portion.

As will be appreciated by skilled artisans from the disclosure provided herein, various attachment mechanisms can be used. For example, the sensor cover can be attached with an adhesive. In certain embodiments, a restorable adhesive can be used to facilitate reattachments of the sensor cover. The restorable adhesive layer can be rejuvenated by application of alcohol to the adhesive. The cover can then be reattached to the sensor. This can be useful where the sensor is moved to a new location or tissue site because the cover can prevent the sensor from taking false readings while the sensor is moved. In some embodiments, no adhesive is used on the sensor cover to leave no residue. In some embodiments, the sensor cover can be made from static cling vinyl, plastic film, or other "clingy" material with no adhesive used. In some embodiments, the sensor cover can be attached through static electricity allowing the cover to cling to the sensor without any adhesive and/or allowing the sensor cover to be reapplied. In other configurations, the sensor cover can be attached with Velcro, fasteners, tabs, clips, slots, or the like.

As will also be appreciated by skilled artisans from the disclosure provided herein, the sensor cover can be detached in various ways. In some embodiments, the sensor cover can be peeled off from the sensor before the sensor is placed at a measurement site. In some embodiments, the sensor can be pulled off from the sensor after placement by pulling on a protruding portion. Depending on the attachment mechanism, the detachment of the sensor cover can expose an adhesive layer or can leave no adhesive residue on the sensor. In some embodiments, the sensor cover can be unclipped or unhooked.

In certain embodiments, the sensor covers are reusable. For example, the sensor cover can be reused if the sensor is temporarily removed for repositioning or for cleaning. The sensor cover can also be replaced on the sensor when the sensor is no longer in use. In some embodiments, the sensor covers are disposable and are disposed of once removed from the sensor.

Although disclosed with reference to the sensor of FIG. 1, an artisan will recognize from the disclosure herein a wide variety of oximeter sensors, optical sensors, noninvasive sensors, medical sensors, or the like that may benefit from the sensor cover disclosed herein. In various embodiments, the sensor can be adapted to receive a tissue site other than a finger such as a, toe, ear lobe, nose, hand, foot, neck, or other site having pulsatile blood flow which can be penetrated by light from the emitter. In addition, the sensor cover 140 can be used with a portable monitor and associated sensor components in certain embodiments. Such monitors, including the sensor components, can be integrated into a hand-held device such as a PDA and typically do not include cables or separate monitors. Portable monitors are often used by first responders in emergency situations, in part because of their portability and ease of use. As such, sensor covers 140 which can protect the sensor components according to embodiments herein can be of particular benefit when used with spot-check monitors.

FIGS. 2A-2C are top cover-attached, top cover-detached, and bottom cover-attached perspective views, respectively, of the sensor cover and sensor of FIG. 1. FIG. 2D illustrates a first 140 and second 240 sensor covers placed over the detector 210 and emitters 230, respectively. FIG. 2A illustrates a view of a side of the sensor placed in contact with a tissue site. In FIG. 2A, the sensor cover 140 attaches to the sensor 120 and covers the detector 210, with a protruding portion 220 extending past the sensor. The sensor cover 140 can be a generally elongated shape made of an opaque material. In an embodiment, one side of the sensor cover can include an adhesive layer over the portion of the cover designed to block the detector 210 while the remainder of the cover can be adhesive free. Thus, the cover 140 does not catch on other objects and cause the cover 140 to be prematurely removed. The cover 140 can be removed by pulling on the protruding portion 220 either before or after the sensor 120 has been placed onto a measurement site. FIG. 2B illustrates the sensor 120 with the sensor cover 140 removed. FIG. 2C illustrates a view of an opposite side of the sensor of FIG. 2A.

Figure 3A:
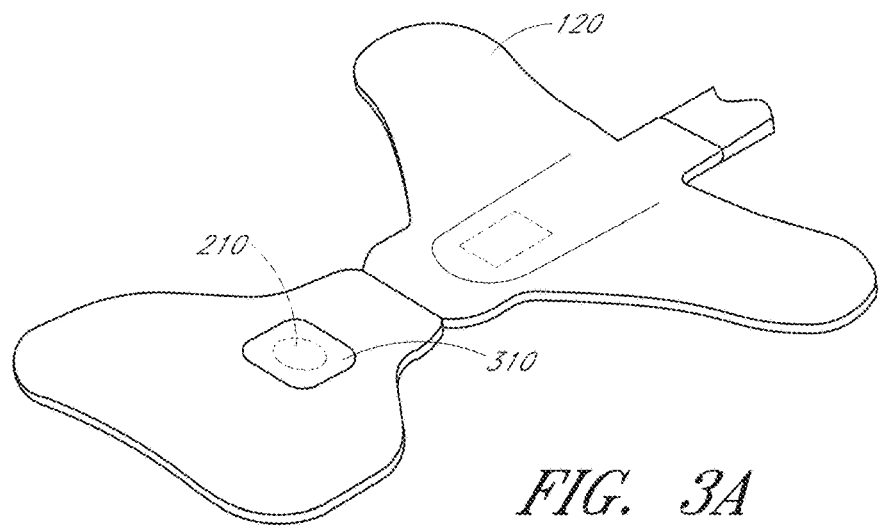
FIG. 3A illustrates a non-protruding sensor cover according to an embodiment of the disclosure.

FIG. 3A illustrates a non-protruding sensor cover 310 according to an embodiment of the disclosure. The opaque sensor cover 310 fits within the sensor 120 and blocks a sensor component 210, such as the emitters or the detector. By staying within the sensor edges, the chance of accidental removal of the cover can be reduced. When the sensor 120 is ready for use, the sensor cover 310 can be removed.

Figure 3B:
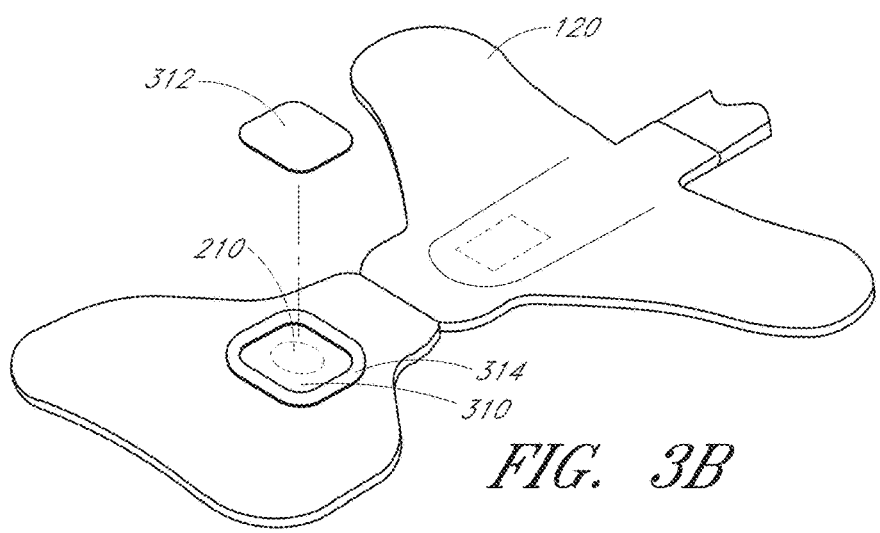
FIG. 3B illustrates a non-protruding sensor cover having an opaque border and a removable opaque center according to an embodiment of the disclosure.

FIG. 3B illustrates a non-protruding sensor cover having an opaque border 314 and a removable opaque center 312. The opaque center 312 can be removed separately from the opaque border 314, leaving an opaque material surrounding the sensor component 210. When the sensor is attached to the patient, the opaque border 314 can minimize light piping, thereby increasing accuracy of the readings. For example, the opaque border 314 can prevent reflected or scattered light that has not passed through tissue from entering into the detector and/or prevent the detector from picking up light from the emitters that fall around instead of on the detector. In an embodiment, the sensor cover can have adhesive on one both sides. Adhesive on both sides of the sensor cover allows the cover to stick to a patient, further preventing light piping or movement of the sensor. In an embodiment the sensor cover can have a clear window section in addition to or instead of a removable center 312.

Figure 3C:
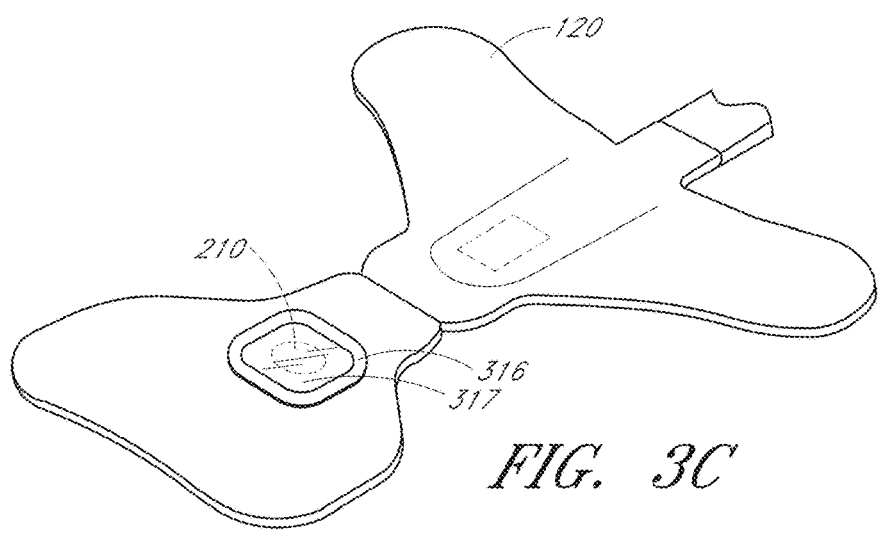
FIG. 3C illustrates a sensor cover having a clear "window" according to an embodiment of the disclosure.

FIG. 3C illustrates a sensor cover 316 having a clear "window" 317 over the sensor component. In an embodiment, the sensor cover can be used to protect the sensor component, provide a new adhesive layer, and/or reduce light piping while allowing the light through the "window." By using a clear window, the sensor cover does not have to be removed when sensor is attached to the patient. In some embodiments, a removable opaque portion can be placed over the window.

Figure 3D:
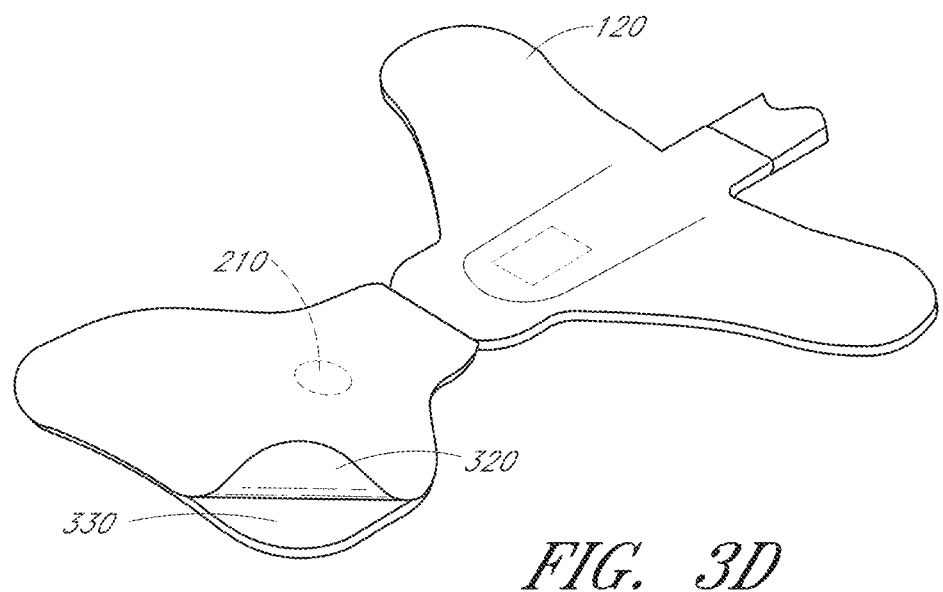
FIG. 3D illustrates a sensor cover integrated with an adhesive cover according to an embodiment of the disclosure.

FIG. 3D illustrates a sensor cover integrated with an opaque adhesive cover 320 for the sensor. An adhesive sensor generally has one or more adhesive covers 320 covering one or more adhesive portions 330 of the sensor. In FIG. 3D, the opaque adhesive cover 320 is extended to cover the sensor component 210. The adhesive cover 320 can be peeled off to reveal the adhesive layer 330 and uncover the sensor component 210.

Figure 3E:
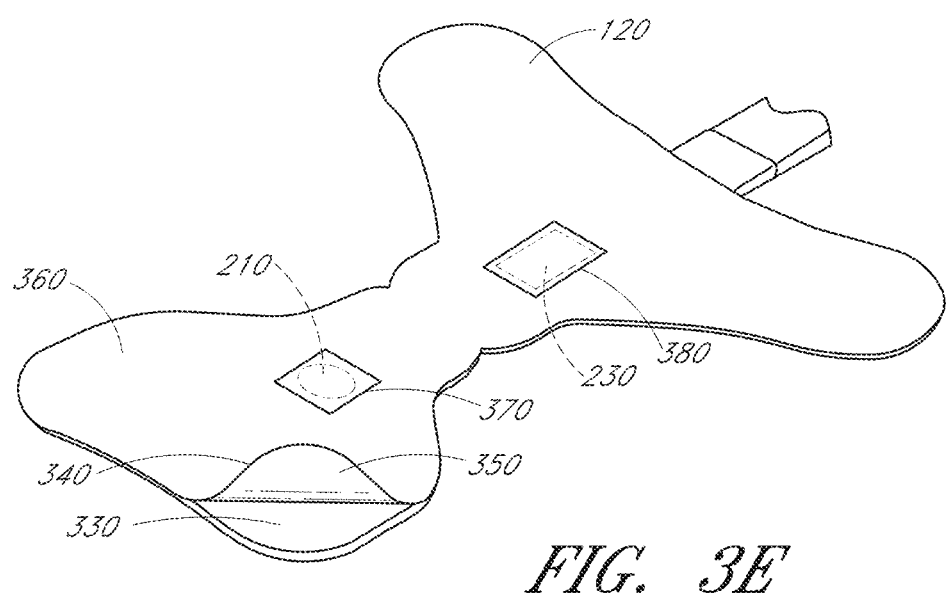
FIG. 3E illustrates a sensor cover covering an adhesive sensor according to an embodiment of the disclosure.

FIG. 3E illustrates a sensor cover 340 covering an adhesive sensor. In FIG. 3E, the opaque sensor cover 340 has adhesive material on both sides of the sensor cover in order to allow reattachment of a sensor where the original adhesive material 330 has lost its adhesiveness. The sensor cover 340 can be placed on the sensor using a first adhesive layer 350 while the sensor is detached from a patient. An adhesive cover (not shown) protects a second adhesive layer 360 and can be removed before the sensor is placed on the patient. The second adhesive layer allows the sensor to be reattached to the patient. The sensor cover can cover both the detector and emitters of the sensor. The sensor cover 322 can have removable or clear sections 370, 380 over the detector and/or emitters to allow light to pass through.

Figure 4A:
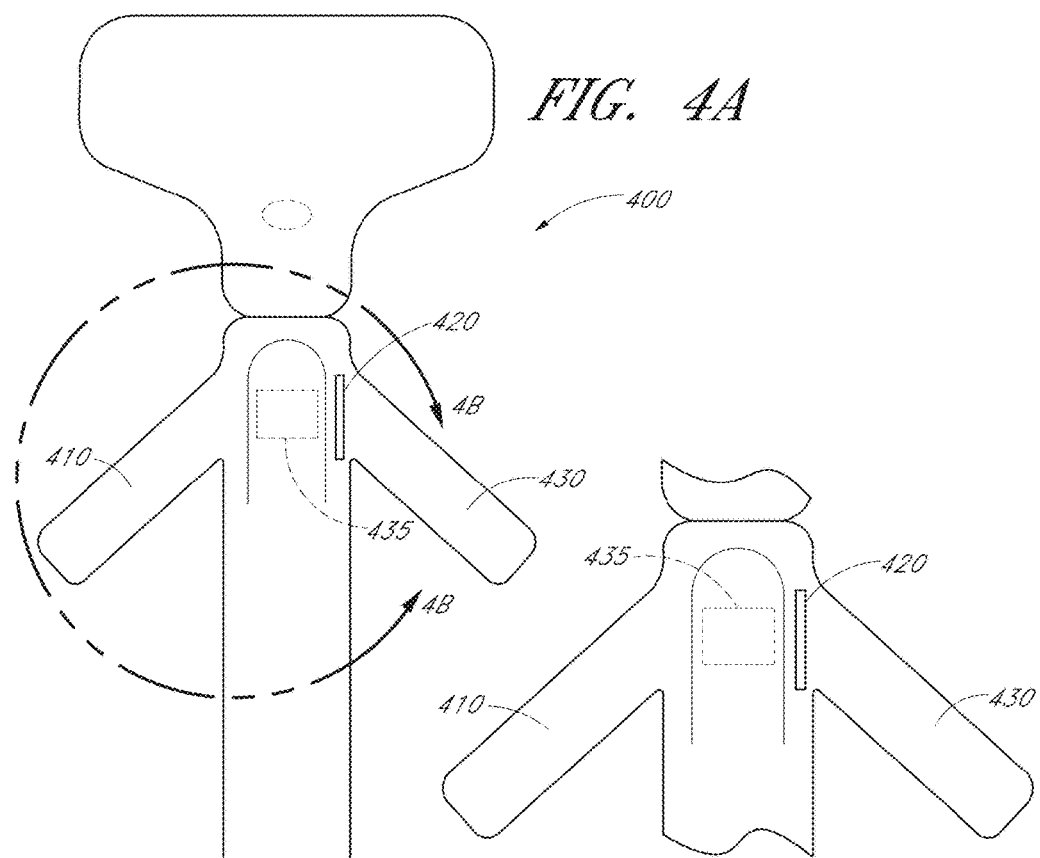
FIGS. 4A-4B are a top view and a close up view, respectively, of an integrated sensor cover according to an embodiment of the disclosure.
Figure 4B:
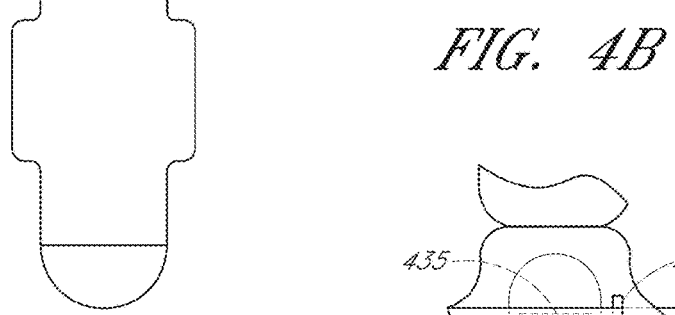
Figure 4C:
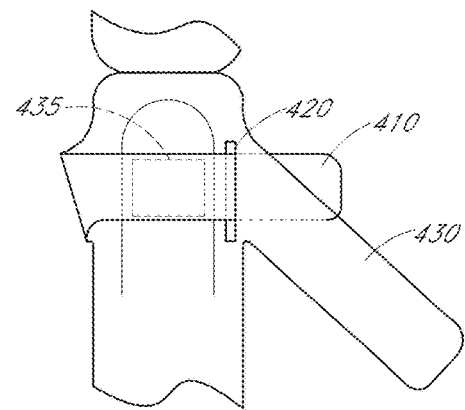
FIG. 4C illustrates the sensor cover of FIGS. 4A-4B covering a sensor component.

FIGS. 4A-4B are a top view and a close up view, respectively, of an integrated sensor cover according to an embodiment of the disclosure. FIG. 4A illustrates an embodiment of the sensor cover where the sensor cover 410 is integrated with the sensor 400. The sensor has a slot 420 positioned near an emitter or a detector. The slot allows an arm 410, 430 to be folded over a sensor component 435, which can be the emitters or the detector, thereby covering it. In certain embodiments, the sensor 400 is an adhesive sensor. The use of a slot allows an adhesive arm 410 to be used as a sensor cover without having to remove the arm's adhesive cover. Once a patient is available, the adhesive arm 410 can be removed from the slot, the adhesive cover can be removed, and the adhesive arms 410, 430 used to secure the adhesive sensor to the patient. FIG. 4B illustrates a close up view of the slot 420 and sensor cover 410 of FIG. 4A. FIG. 4C illustrates the sensor cover 410 folded over the sensor component 435 with the end of the sensor cover inserted into the slot. A portion of the sensor cover extends into the slot and to the back side of the sensor. The slot keeps the sensor cover 410 generally secure against the sensor component 435.

Figure 5A:
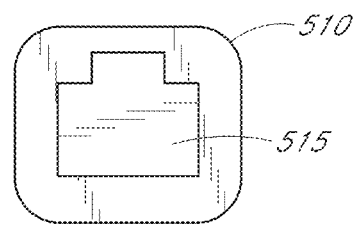
FIG. 5A is a front view a sensor cover attachable to a reusable sensor according to an embodiment of the disclosure.
Figure 5B:
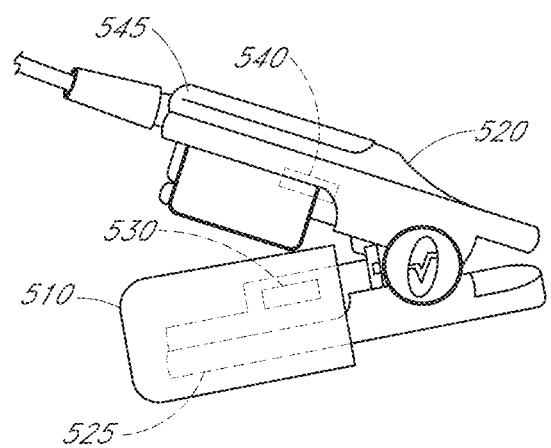
FIG. 5B illustrates the mating of the sensor cover of FIG. 5A with a sensor.

FIG. 5A is a front view a sensor cover 510 attachable to a reusable sensor according to an embodiment of the disclosure. The sensor cover 510 includes a recess 515 into which a sensor housing can be inserted. The sensor housing generally fits closely in the recess 515. Friction between the inner surfaces of the sensor cover 510 and the sensor housing generally secures the housing with the sensor cover 510. FIG. 5B illustrates the mating of the sensor cover 510 of FIG. 5A with a sensor 520. In the illustrated embodiment, the sensor 520 is a reusable clip-style sensor. The sensor cover 510 fits over a lower sensor housing 525. The sensor housings 525, 545 can contain sensor components 530, 540, such as the emitters or the detector. In certain embodiments, the sensor component 530 is a detector and the sensor cover 510 prevents the detector from receiving light. The sensor cover 510 can be removed when the sensor 520 is in use and reattached once the sensor 520 is not in use.

Figure 6:
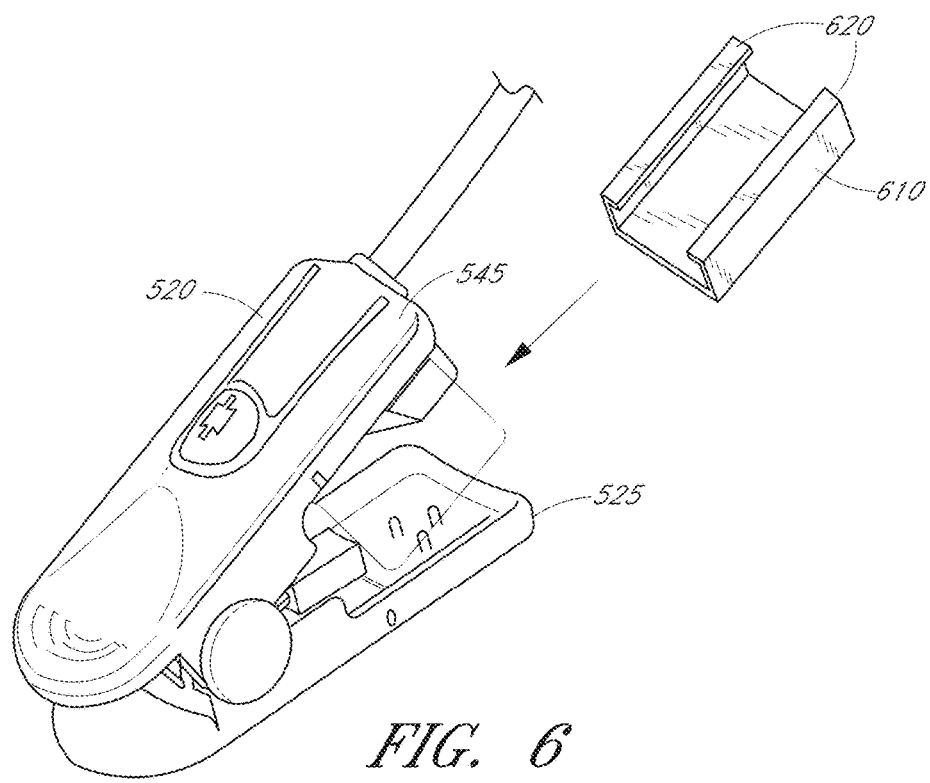
FIG. 6 illustrates a sensor cover attachable to a sensor via one or more tabs according to an embodiment of the disclosure.

FIG. 6 illustrates a sensor cover 610 attachable to a sensor 520 via one or more tabs or attachment arms 620 according to an embodiment of the disclosure. The tabs 620 fit over the sides of an upper housing 545 of the sensor and generally secure the sensor cover 610 against the upper housing 545. The sensor cover 610 covers the sensor component, such as the emitters or the detector, located in the upper housing 545.

Figure 7:
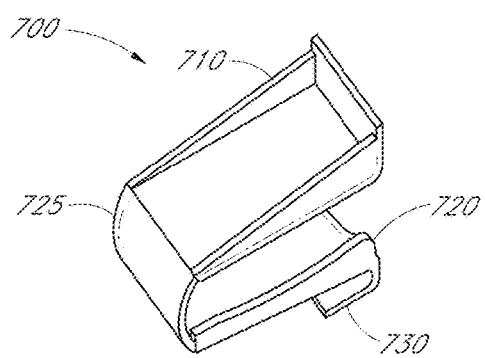
FIG. 7 illustrates a sensor cover configured to block both the emitters and the detector according to an embodiment of the disclosure.

FIG. 7 illustrates an embodiment of the sensor cover 700 configured to block both the emitters and the detector. An upper arm 710 secures against an upper housing of a sensor. A lower arm 720 secures against a lower housing of a sensor. The upper 710 and lower 720 arms are connected by a hinge portion 725. The arms 710, 720 can be attached via a press fit. The lower arm 720 can also include an attachment arm 730 to better secure the sensor cover 700 against the lower housing of the sensor.

Figure 8:
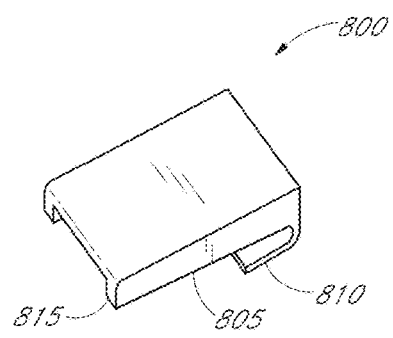
FIG. 8 illustrates a sensor cover attachable to a sensor via an attachment arm according to an embodiment of the disclosure.

FIG. 8 illustrates an embodiment of the sensor cover 800 attachable to a sensor housing via an attachment arm 810. The attachment arm 810 is configured to secure the sensor cover 800 in place when applied to the sensor. Upon application to a sensor, the front portion of the sensor housing may occupy the space defined by the attachment arm 810 and the underside of the lower portion 805 of the sensor cover 800. The attachment arm 810 helps to releasably secure the sensor, via a friction fit, for example. One or more other features, such as the lip 815 disposed on the side of the sensor cover proximal to the sensor can be included to further secure the sensor cover 800 in the sensor. Upon insertion of the sensor cover 800 into the sensor, the sides of the sensor housing abut the lip 815. Accordingly, the lip 815 can help ensure that the sensor cover 800 is positioned appropriately deep within the sensor.

Although the above embodiments have been described with respect to an opaque material intended to optically insulate the optical sensor, as will be appreciated by skilled artisans from the disclosure provided herein, sensor covers made of different insulative materials can be used as appropriate for different types of sensors. For example, sonically insulative materials, such as foam, rubber, cotton, and/or other sound deadening materials can be used to cover sensors that employ sound, such as a bioacoustic or ultrasound sensor. In some embodiments, electrically insulative materials, such as rubber, polyethylene, silicone and/or other insulators can be used to cover sensors that employ electrical signals, such as bioimpedance sensors. In some embodiments, mechanically insulative materials, such as hard plastic, metal, rubber, silicone, and/or other rigid or dampening materials can be used to cover mechanical sensors to prevent sensor actuation. In some embodiments, chemically insulative material, such as plastic, metal, polyethylene or the like can be used to cover chemical sensors and prevent their exposure to the environment.

Figure 9D:
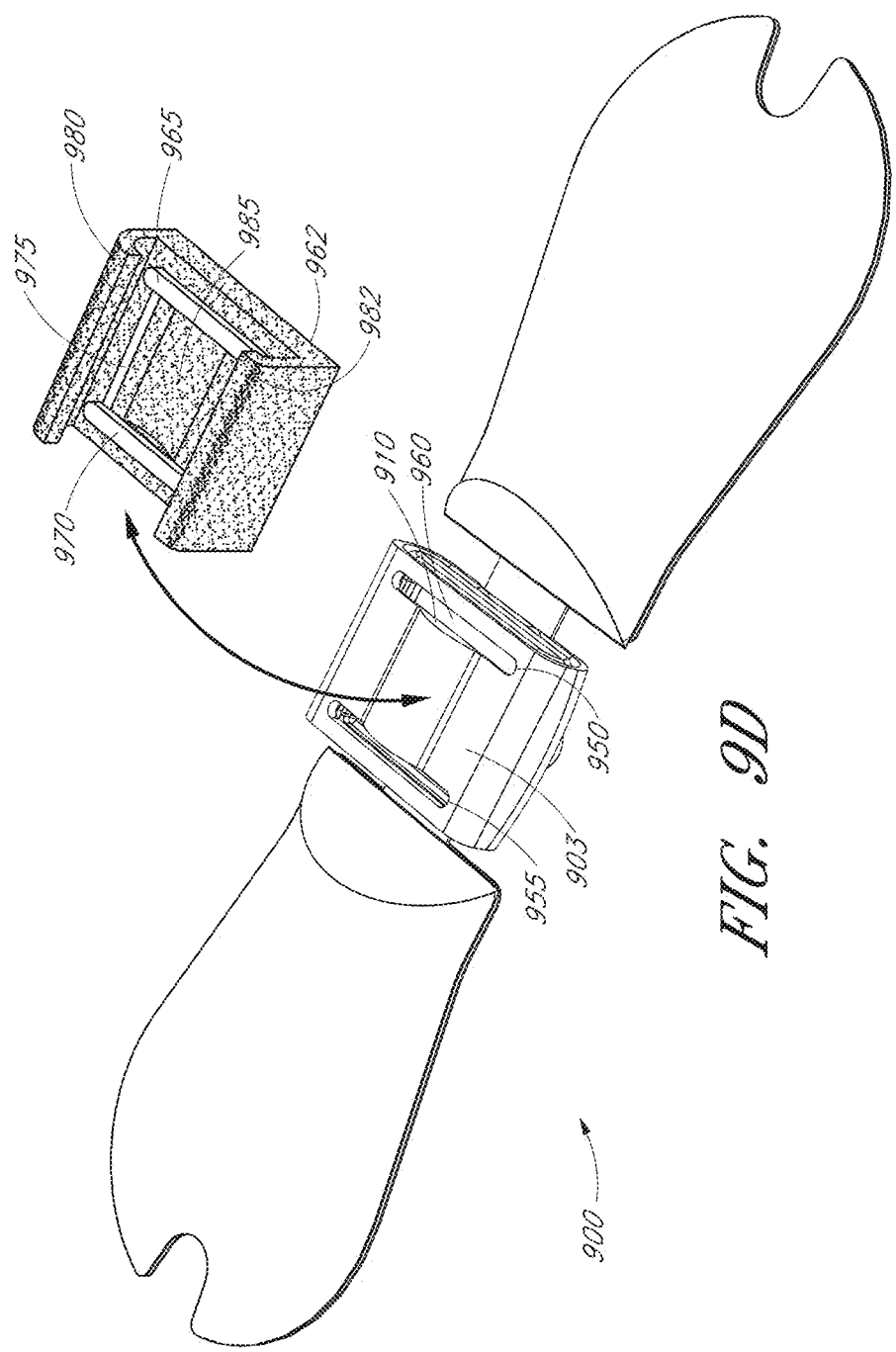

FIGS. 9A-9D illustrate embodiments of sensor covers for a bioacoustic sensor. FIG. 9A illustrates one embodiment of a bioacoustic sensor. The bioacoustic sensor 900 is configured for placement against a patient's skin. The contact surface 903 of the sensor 900 is placed against the skin. The bioacoustic sensor picks up sound waves from the patient's body and converts them into electrical signals for transmission to a monitoring device. In one embodiment, the bioacoustic sensor can use a piezoelectric transducer as the sensing element to detect sound waves. In FIG. 9A a sensor cover 905 made of a sound-deadening material, such as foam, rubber, and/or cotton, is attached to the contact surface to prevent sound waves from being detected by the bioacoustic sensor 900. The sound-deadening material can be attached by adhesive, tabs, clips, friction fit, and/or other connection mechanism. In FIG. 9A, the bioacoustic sensor has a bump 910 on the contact surface 903 positioned to apply pressure to the sensing element so as to bias the sensing element in tension and improve the receptivity of the sensing element to sound waves. Where such a bump 910 exists on the contact surface 903 of the sensor, embodiments of sensor cover 905 can be provided with a corresponding recess.

FIG. 9B illustrates an embodiment of the sensor cover 920 made of shaped sound-deadening material to increase the surface area available to absorb sound. In one embodiment, a plurality of wedge shaped protrusions 925 is formed on the surface of the sensor cover 920. In other embodiments, different shaped protrusions can be used, such as waveform, pyramid, egg crate, and/or other shapes to increase the surface area.

FIG. 9C illustrates a bioacoustic sensor cover having one or more attachment arms according to an embodiment of the disclosure. An attachment arm 935 is configured to releasably secure the sensor cover 930 when applied to the sensor via a friction fit, for example. A second attachment arm 936 can be provided to further secure the sensor cover 930 to the sensor 900. A recess 940 can also be formed on the interior surface of the sensor cover 930 in order to conform to protrusions on the contact surface of the sensor 900. Where the contact surface of the sensor 900 is flat, the interior surface can also be flat.

FIG. 9D illustrates a bioacoustic sensor having conductive leads according to an embodiment of the disclosure. In FIG. 9D, the illustrated bioacoustic sensor 900 has one or more apertures 950, 955 exposing the sensing element 960 to the contact surface 903. In one embodiment, the sensor cover 962 prevents the bioacoustic sensor from taking readings by creating an electrical short in the sensor. One or more conductive leads or wires 965, 970 configured to fit into the apertures 950, 955 in the sensor housing are disposed on the sensor cover 962. The conductive leads 965, 970 abut the negative and positive electrical poles of the sensing element 960. The conductive leads can be formed of copper or other conductive material. In one embodiment, the conductive leads 965, 970 can abut internal wiring that connects to the negative and positive electrical poles, such that a direct connection is not required. The conductive leads 965, 970 are joined by a connector lead or wire 975 to generate a short circuit in the sensor 900. In an embodiment, the conductive leads 965, 970 and connector lead 975 are a single connected structure. In an embodiment, the sensor cover 962 further comprises one or more attachment arms 980, 982 for releasably securing the sensor cover 962 to the sensor 900. In an embodiment, the sensor cover 962 further comprises a recess 985 to conform against a protrusion 910 on the contact surface 903 of the sensor. In one embodiment, the sensor cover 962 is formed out of a sound deadening material, such as foam or rubber. In one embodiment, the sensor cover 962 is made of hard plastic or other types of plastic materials.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Various sensor covers have been disclosed in detail in connection with various embodiments. These embodiments are disclosed by way of examples only and are not to limit the scope of the claims that follow. One of ordinary skill in the art will appreciate the many variations, modifications and combinations. For example, in various embodiments, adhesive, snap-fit, friction-fit, clips, tabs, and other attachment mechanisms can be employed. In addition, in various embodiments the sensor covers are used with a sensor that can measure any type of physiological parameter. In various embodiments, the sensor covers can be for any type of medical device or sensor. In various embodiments, adhesive can be placed on both sides of the sensor cover to aid in the reattachment of sensors where the sensor adhesive has grown weak. In various embodiments, sensors covers can be made in whole or in part of materials such as foam, polyester, polypropylene, rubber, vinyl, cling vinyl, urethane rubber plastic or other plastic materials, cloth, metal, combinations of the same or the like.

What is claimed is:

1. A method of providing a sensor cover for a noninvasive physiological sensor, the method comprising:
    providing a sensor cover comprising:
        an opaque portion attachable over a sensing portion of the sensor, the opaque portion configured to prevent the sensing portion from measuring a physiological variable; and
        a connector for attaching the sensor cover to a sensor; and
    attaching the sensor cover to the sensor, the sensor cover removable from the sensor,
    wherein the connector comprises one or more attachment arms.

2. The method of claim 1, wherein the opaque portion is made of a sound-deadening material, the sound-deadening material configured to prevent the sensing portion of the sensor from measuring sound waves.

3. The method of claim 1, wherein the opaque portion is made of an insulating material, the insulating material configured to prevent the sensing portion of the sensor from measuring electrical signals.

4. The method of claim 1, wherein the connector further comprises a surface of the cover frictionally engageable with the sensor.

5. The method of claim 1, wherein the sensor is at least one of a pulse oximeter sensor, an acoustic sensor, or a bioimpedance sensor.

6. The method of claim 1, wherein the sensor is a clip-type sensor.

7. A method of providing a sensor cover for a noninvasive physiological sensor, the method comprising:
    providing a sensor cover comprising:
        an opaque portion attachable over a sensing portion of the sensor, the opaque portion configured to prevent the sensing portion from measuring a physiological variable;
        a connector for attaching the sensor cover to a sensor; and
        one or more conductive leads disposed on the opaque portion, the conductive leads configured to generate a short circuit in the sensor; and
    attaching the sensor cover to the sensor, the sensor cover removable from the sensor.

8. The method of claim 7, wherein the opaque portion is made of a sound-deadening material, the sound-deadening material configured to prevent the sensing portion of the sensor from measuring sound waves.

9. The method of claim 7, wherein the opaque portion is made of an insulating material, the insulating material configured to prevent the sensing portion of the sensor from measuring electrical signals.

10. The method of claim 7, wherein the connector further comprises a surface of the cover frictionally engageable with the sensor.

11. The method of claim 7, wherein the sensor is at least one of a pulse oximeter sensor, an acoustic sensor, or a bioimpedance sensor.

12. The method of claim 7, wherein the sensor is a clip-type sensor.

13. A method of providing a sensor cover for a noninvasive physiological sensor, the method comprising:
    providing a sensor cover comprising:
        an opaque portion attachable over a sensing portion of the sensor, the opaque portion configured to prevent the sensing portion from measuring a physiological variable; and
        a connector for attaching the sensor cover to a sensor;
    attaching the sensor cover to the sensor, the sensor cover removable from the sensor,
    wherein the sensor is an adhesive sensor having a flexible substrate and an adhesive layer, and
    wherein the opaque portion is an elongate protrusion integrated with the flexible substrate, wherein the connector is slot disposed on the flexible substrate for receiving the protrusion, and wherein placing the protrusion within the slot attaches the protrusion over the sensing portion.

* * * * *